(12) United States Patent
Seth et al.

(10) Patent No.: US 7,883,769 B2
(45) Date of Patent: *Feb. 8, 2011

(54) INTEGRALLY FOAMED MICROSTRUCTURED ARTICLE

(75) Inventors: Jayshree Seth, Woodbury, MN (US); Christopher K. Haas, Cottage Grove, MN (US); Ravi K. Sura, Woodbury, MN (US); Katherine A. S. Graham, Roseville, MN (US); Janet A. Venne, Roseville, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/464,215

(22) Filed: Jun. 18, 2003

(65) Prior Publication Data

US 2004/0258902 A1    Dec. 23, 2004

(51) Int. Cl.
*B32B 3/26* (2006.01)
*B32B 3/06* (2006.01)

(52) U.S. Cl. .............. 428/314.8; 428/314.4; 428/316.6; 428/99; 428/100

(58) Field of Classification Search .............. 428/316.6, 428/99, 100, 315.7, 314.4, 314.8
See application file for complete search history.

(56) References Cited

U.S. PATENT DOCUMENTS

| 4,290,248 | A | 9/1981 | Kemerer et al. |
| 4,473,665 | A | 9/1984 | Martini-Vvedensky et al. |
| 4,714,716 | A | 12/1987 | Park |
| 4,753,838 | A | 6/1988 | Kimura |
| 4,761,256 | A | 8/1988 | Hardenbrook et al. |
| 4,916,198 | A | 4/1990 | Scheve et al. |
| 4,940,736 | A | 7/1990 | Alteepping et al. |

(Continued)

FOREIGN PATENT DOCUMENTS

EP    0830930 A1    3/1998

(Continued)

OTHER PUBLICATIONS

Ainslie T. Young, "Microcellular Foams Via Phase Separation", J. Vac. Sci. Technol. A 4(3), p. 1128-1133, May/Jun. 1986.*

(Continued)

*Primary Examiner*—Hai Vo

(57) ABSTRACT

The invention is directed in part to an article that includes a polymer foam having a surface with surface microstructures, the surface microstructures have at least one extent or dimension of about 10 microns or more, preferably 50 microns or more. A maximum extent (unless it is a continuous rib-like structure) the microstructure is about 300 microns or less, preferably 200 microns or less, and generally a maximum height of 1000 microns or less, preferably 750 microns or less and a minimum height of 200 microns or more, preferably 300 microns or more. The foamed article may be provided in a variety of shapes, including a rod, a cylinder, a sheet, etc. In a preferred embodiment where the foam is provided in the form of a sheet, the foam has a pair of major surfaces, one or both of which can be provided with surface microstructures. The foam backing and microstructures include a plurality of voids, which voids are preferably of a mean size substantially less than the smallest cross-sectional dimension or extent of the microstructures.

21 Claims, 6 Drawing Sheets

U.S. PATENT DOCUMENTS

| | | | |
|---|---|---|---|
| 5,334,359 A | | 8/1994 | Masutomi et al. |
| 5,491,015 A | * | 2/1996 | Reeves et al. ............... 428/167 |
| 5,558,658 A | * | 9/1996 | Menard et al. ......... 604/385.23 |
| 5,599,602 A | | 2/1997 | Leonard et al. |
| 5,605,936 A | | 2/1997 | DeNicola, Jr. et al. |
| 5,824,400 A | | 10/1998 | Petrakis et al. |
| 6,096,247 A | * | 8/2000 | Ulsh et al. .................... 264/2.7 |
| 6,106,922 A | | 8/2000 | Cejka et al. |
| 6,174,476 B1 | | 1/2001 | Kennedy et al. |
| 6,174,930 B1 | * | 1/2001 | Agarwal et al. ............. 521/134 |
| 6,280,824 B1 | * | 8/2001 | Insley et al. ................. 428/172 |
| 6,353,037 B1 | * | 3/2002 | Thunhorst et al. ............. 521/64 |
| 6,406,466 B1 | | 6/2002 | Pozniak |
| 6,423,252 B1 | * | 7/2002 | Chun et al. .................... 264/28 |
| 6,497,946 B1 | * | 12/2002 | Kretman et al. .......... 428/317.9 |
| 6,540,497 B1 | | 4/2003 | Fuda et al. |
| 6,890,642 B2 | * | 5/2005 | Kaminsky et al. ........ 428/319.3 |
| 7,001,702 B2 | * | 2/2006 | Cheng et al. ............. 430/109.3 |
| 7,185,401 B2 | * | 3/2007 | Ausen et al. ................... 24/451 |
| 2002/0162197 A1 | | 11/2002 | Romanko et al. |
| 2003/0011092 A1 | * | 1/2003 | Tan et al. ....................... 264/51 |
| 2003/0104192 A1 | * | 6/2003 | Hester et al. |
| 2003/0105176 A1 | * | 6/2003 | Haas et al. |
| 2003/0209642 A1 | * | 11/2003 | Fontana et al. ......... 248/231.91 |
| 2004/0253412 A1 | * | 12/2004 | Dotson ....................... 428/119 |

FOREIGN PATENT DOCUMENTS

| | | |
|---|---|---|
| EP | 0892320 A2 | 1/1999 |
| WO | 98/39759 | 9/1998 |
| WO | 99/17630 | 4/1999 |
| WO | 99/17631 | 4/1999 |
| WO | WO 99/36466 | 7/1999 |
| WO | WO 99/61520 | 12/1999 |
| WO | WO 00/00520 | 1/2000 |
| WO | 00/06974 | 10/2000 |
| WO | WO 02/00412 A2 | 1/2002 |
| WO | WO 2004/093591 | 11/2004 |

OTHER PUBLICATIONS

Seymour S. Schwartz & Sidney H. Goodman, Plastics Materials and Processes, p. 9, Van Nostrand Reinhold Publishing Company, Copyright 1982.

* cited by examiner

INTEGRALLY FOAMED MICROSTRUCTURED ARTICLE

BACKGROUND OF THE INVENTION

This invention relates to preparing extruded articles having surface microstructures formed with a microcellular polymer foam. Generally, a polymer foam includes a polymer matrix and is characterized by a density that is lower than the density of the polymer matrix itself. Density reduction is achieved in a number of ways, including through creation of gas-filled voids in the matrix (e.g., by means of a blowing agent). The foam void is of a size less than that of the microstructures.

In order to improve the mechanical properties of standard cellular foamed materials, a microcellular process was developed for manufacturing foamed plastics having greater cell densities and smaller cell sizes. Such a process is described, for example, in U.S. Pat. No. 4,473,665. The process presaturates the plastic material with a uniform concentration of a gas under pressure. A sudden induction of thermodynamic instability then nucleates a large number of cells. For example, the material is presaturated with the gas and maintained under pressure at its glass transition temperature. The material is suddenly exposed to a low pressure to nucleate cells and promote cell growth to a desired size, depending on the desired final density, thereby producing a foamed material having microcellular voids, or cells, therein. The material is then quickly further cooled, or quenched, to maintain the microcellular structure. Such a technique tends to increase the cell density, i.e., the number of cells per unit volume of the parent material, and to produce much smaller cell sizes than those in standard cellular structures. The resulting microcellular foamed materials that are produced, using various thermoplastics and thermosetting plastics, tend to have average cell sizes in the range of 3 to 10 microns, with void fractions of up to 50% of the total volume and maximum cell densities of about one billion voids per cubic centimeter of the parent material.

Microcellular foamed plastic materials are also described in U.S. Pat. No. 4,761,256 which describes a web of plastic material impregnated with an inert gas. The web is reheated at a foaming station to induce foaming, the temperature and duration of the foaming process being controlled prior to the generation of the web to produce the desired characteristics. The process is designed to provide for production of foamed plastic web materials in a continuous manner. The cell sizes in the foamed material is stated to be within a range of from 2 to 9 microns in diameter.

U.S. Pat. No. 5,334,359 describes foamed materials which can be of smaller cell sizes, e.g., 1.0 micron or less. The materials also allegedly have a wide range of void fraction percentages from very high void fractions (low material densities) up to 90%, or more, to very low void fractions (high material densities) down to 20%, or less.

SUMMARY OF THE INVENTION

Figure 1:
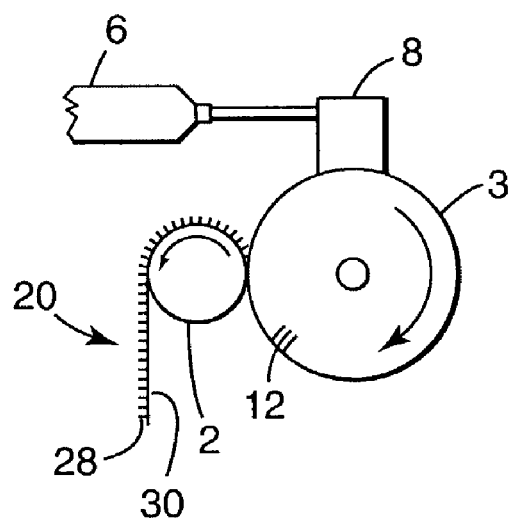
FIG. 1 is a schematic view of a first method for forming an extruded foamed hook strip in accordance with the invention.

In a first aspect, the invention is directed to an article that includes a polymer foam having a surface with surface microstructures. The surface microstructures have at least one extent or dimension of about 10 microns or more, preferably 50 microns or more, and preferably a maximum extent (unless it is a continuous rib-like structure) of about 300 microns or less, preferably 200 microns or less, and generally a maximum height of 1000 microns or less, preferably 750 microns or less and a minimum height of 200 microns or more, preferably 300 microns or more. The foamed article may be provided in a variety of shapes, including a rod, a cylinder, a sheet, etc. In a preferred embodiment where the foam is provided in the form of a sheet, the foam has a pair of major surfaces, one or both of which can be provided with surface microstructures. The foam backing and microstructures include a plurality of discrete foam cells, which foam cells are of a mean size substantially less than the smallest cross-sectional dimension or extent of the microstructures. The foam can be formed by known blowing agents.

DETAILED DESCRIPTION OF THE PREFERRED EMBODIMENT

The shape of the foam is dictated by the shape of die and/or the mold surface if used. Although a variety of shapes may be produced, the foam is typically produced in the form of a continuous or discontinuous sheet having surface microstructures.

An extrusion process using a single-screw, double-screw or tandem extrusion system may also be used to form the foam using a blowing agent, e.g., a physical or chemical blowing agent. The temperature and pressure conditions in the extrusion are preferably sufficient to maintain the polymeric material and blowing agent as a homogeneous solution or dispersion. Preferably, the polymeric materials exit the extruder and are foamed at no more than 30° C. above the melting temperature of the neat polymer thereby producing desirable properties such as uniform and/or small cell sizes. When a physical blowing agent, such as $CO_2$ is used, the polymer is generally initially maintained above the melting temperature. The physical blowing agent (preferably in the supercritical state) is then injected (or otherwise mixed) with the molten polymer and the melt mixture is cooled in the extruder preferably to an exit temperature that is less than 50° C. above the melting temperature or $T_g$ of the polymer $T<T_m$ (or $T_g$)+50° C. while the pressure is maintained at or above 1000 psi (13.8 MPa), preferably 30° C. while the pressure is maintained at or above 2000 psi. Under these conditions the polymer/blowing agent generally remains in a single phase. As the melt mixture passes through the die the melt foams and expands, generating foams with preferably small, uniform cell sizes. When a chemical blowing agent is used, the blowing agent is added to the polymer, mixed, heated to a temperature above the $T_m$ of the polymer to ensure intimate mixing and further heated to an activation temperature of the chemical blowing agent, resulting in generation of gasses. The melt mixture is cooled in the extruder preferably in a manner similar to that used for physical blowing agents. A liquid or solid chemical foaming agent is generally added to the polymer prior to its reaching its molten ($T_m$) state.

A supercritical fluid foaming agent can be defined as a material which is maintained at a temperature which exceeds a critical temperature and at a pressure which exceeds a critical pressure so as to place the material in a supercritical fluid state. In such state, the supercritical fluid has properties which cause it to act, in effect, as both a gas and a liquid. Thus, in the supercritical state, such a fluid has the solvent characteristics of a liquid, but the surface tension thereof is substantially less than that of a liquid so that the fluid can diffuse much more readily into a solute material, as in the nature of a gas. For example, it is known that carbon dioxide ($CO_2$) can be placed in a supercritical state when its temperature exceeds 31° C. and its pressure exceeds 1100 psi.

When the foam is formed into a microstructured article directly from the extrusion die, the polymer matrices of the invention foams can comprise one or more amorphous polymers or polymer blends as well as semicrystalline polymer. The polymers may be homopolymers or copolymers, including random and block copolymers. The amorphous polymers have a $T_g$ with the $T_g$ typically an average, (based on the weight percent of each polymer in the mixture), of the glass transition temperatures of the component polymers. Suitable amorphous polymers include, e.g., polystyrenes, polycarbonates, polyacrylics, polymethacrylics, elastomers, such as styrenic block copolymers, e.g., styrene-isoprene-styrene (SIS), styrene-ethylene/butylene-styrene block copolymers (SEBS), polybutadiene, polyisoprene, polychloroprene, random and block copolymers of styrene and dienes (e.g., styrene-butadiene rubber (SBR)), ethylene-propylene-diene monomer rubber, natural rubber, ethylene propylene rubber, polyethylene-terephthalate (PETG). Other examples of amorphous polymers include, e.g., polystyrene-polyethylene copolymers, polyvinylcyclohexane, polyacrylonitrile, polyvinyl chloride, thermoplastic polyurethanes, aromatic epoxies, amorphous polyesters, amorphous polyamides, acrylonitrile-butadiene-styrene (ABS) copolymers, polyphenylene oxide alloys, high impact polystyrene, polystyrene copolymers, polymethylmethacrylate (PMMA), fluorinated elastomers, polydimethyl siloxane, polyetherimides, amorphous fluoropolymers, amorphous polyolefins, polyphenylene oxide, polyphenylene oxide-polystyrene alloys, copolymers containing at least one amorphous component, and mixtures thereof.

When the microstructured article is formed by contact with a mold surface having the microstructures therein the polymer must be maintained in a molten state following extrusion from the die. Amorphous polymers generally freeze immediately and are not preferred for this process. Semicrystalline polymers are preferred. For example, high, medium, low and linear low density polyethylene, fluoropolymers, poly(1-butene), ethylene/acrylic acid copolymer, ethylene/vinyl acetate copolymer, ethylene/propylene copolymer, styrene/butadiene copolymer, ethylene/styrene copolymer, ethylene/ethyl acrylate copolymer, ionomers and thermoplastic elastomers such as styrene/ethylene-butylene/styrene (SEBS), and ethylene/propylene/diene copolymer (EPDM). Preferred are polyolefins such as polypropylenes or polyethylenes and most preferably high melt strength polyolefins, such as branched polyolefins. These high melt strength polymers help control the growth of the multiple discrete foam cells within the desired range necessary for creating the discrete microstructures and prevent collapse of the cells during surface microstructure formation if needed. Suitable semi-crystalline materials include polyethylene, polypropylene, polymethylpentene, polyisobutylene, polyolefin copolymers, Nylon 6, Nylon 66, polyester, polyester copolymers, fluoropolymers, poly vinyl acetate, poly vinyl alcohol, poly ethylene oxide, functionalized polyolefins, ethylene vinyl acetate copolymers, metal neutralized polyolefin ionomers available under the trade designation SURLYN (E.I. DuPont de Nemours, Wilmington, Del.), polyvinylidene fluoride, polytetrafluoroethylene, polyformaldehyde, polyvinyl butyral, and copolymers having at least one semi-crystalline compound. Preferred high melt strength polymers are high melt strength polypropylenes which include homo- and copolymers containing 50 weight percent or more propylene monomer units, preferably at least 70 weight percent, and have a melt strength in the range of 25 to 60 cN at 190° C. Melt strength may be conveniently measured using an extensional rheometer by extruding the polymer through a 2.1 mm diameter capillary having a length of 41.9 mm at 190° C. and at a rate of 0.030 cc/sec; the strand is then stretched at a constant rate while measuring the force to stretch at a particular elongation. Preferably the melt strength of the polypropylene is in the range of 30 to 55 cN, as described in WO 99/61520.

Such high melt strength polypropylenes may be prepared by methods generally known in the art. Reference may be made to U.S. Pat. No. 4,916,198 which describes a high melt strength polypropylene having a chain-hardening elongational viscosity prepared by irradiation of linear propylene in a controlled oxygen environment. Other useful methods include those in which compounds are added to the molten polypropylene to introduce branching and/or crosslinking such as those methods described in U.S. Pat. No. 4,714,716, WO 99/36466 and WO 00/00520. High melt strength polypropylene may also be prepared by irradiation of the resin as described in U.S. Pat. No. 5,605,936. Still other useful methods include forming a bipolar molecular weight distribution as described in JI Raukola, "A New Technology To Manufacture Polypropylene Foam Sheet And Biaxial Oriented Foam Film", VTT Publications 361, Technical Research Center of Finland, 1998 and in U.S. Pat. No. 4,940,736.

Generally, the foamable polypropylenes may comprise solely propylene homopolymer or may comprise a copolymer having 50 wt % or more propylene monomer content. Further, the foamable propylenes may comprise a mixture or blend of propylene homopolymers or copolymers with a homo- or copolymer other than propylene homo- or copolymers. Particularly useful propylene copolymers are those of propylene and one or more non-propylenic monomers. Propylene copolymers include random, block, and grafted copolymers of propylene and olefin monomers selected from the group consisting of ethylene, $C_3$-$C_8$ α-olefins and $C_4$-$C_{10}$ dienes. Propylene copolymers may also include terpolymers of propylene and α-olefins selected from the group consisting of $C_3$-$C_8$ α-olefins, wherein the α-olefin content of such terpolymers is preferably less than 45 wt %. The $C_3$-$C_8$ α-olefins include 1-butene, isobutylene, 1-pentene, 3-methyl-1-butene, 1-hexene, 3,4-dimethyl-1-butene, 1-heptene, 3-methyl-1-hexene, and the like. Examples of $C_4$-$C_{10}$ dienes include 1,3-butadiene, 1,4-pentadiene, isoprene, 1,5-hexadiene, 2,3 dimethyl hexadiene and the like.

If high melt strength polymers are used, minor amounts (less than 50 percent by weight) of amorphous polymers may be added to the high melt strength polymer. Suitable amorphous polymers include, e.g., polystyrenes, polycarbonates, polyacrylics, polymethacrylics, elastomers, such as styrenic block copolymers, e.g., styrene-isoprene-styrene (SIS), styrene-ethylene/butylene-styrene block copolymers (SEBS), polybutadiene, polyisoprene, polychloroprene, random and block copolymers of styrene and dienes (e.g., styrene-butadiene rubber (SBR)), ethylene-propylene-diene monomer rubber, natural rubber, ethylene propylene rubber, polyethylene-terephthalate (PETG). Other examples of amorphous polymers include, e.g., polystyrene-polyethylene copolymers, polyvinylcyclohexane, polyacrylonitrile, polyvinyl chloride, thermoplastic polyurethanes, aromatic epoxies, amorphous polyesters, amorphous polyamides, acrylonitrile-butadiene-styrene (ABS) copolymers, polyphenylene oxide alloys, high impact polystyrene, polystyrene copolymers, polymethylmethacrylate (PMMA), fluorinated elastomers, polydimethyl siloxane, polyetherimides, amorphous fluoropolymers, amorphous polyolefins, polyphenylene oxide, polyphenylene oxide—polystyrene alloys, copolymers containing at least one amorphous component, and mixtures thereof.

In addition to the high melt strength polypropylene, the foam layer may contain other added components such as dyes, particulate materials, a colorant, an ultraviolet absorbing material, inorganic additives, and the like. Useful inorganic additives include glass fibers, $TiO_2$, $CaCO_3$, mica or high aspect ratio clays such as wollastonite Either a physical or chemical blowing agent may plasticize, i.e., lower the $T_m$ and $T_g$ of, the polymeric material. With the addition of a blowing agent, the melt mixture may be processed and foamed at temperatures considerably lower than otherwise might be required, and in some cases may be processed below the melt temperature of the polypropylene. The lower temperature can allow the foam to cool and stabilize (i.e., reach a point of sufficient solidification to arrest further cell growth and produce smaller and more uniform cell sizes).

Physical blowing agents useful in the present invention may be any materials that are a vapor at the temperature and pressure at which the foam exits the die. A physical blowing agent may be introduced, i.e., injected into the polymeric material as a gas or supercritical fluid. Flammable blowing agents such as pentane, butane and other organic materials may be used, but non-flammable, non-toxic, non-ozone depleting blowing agents such as carbon dioxide, nitrogen, water, $SF_6$, nitrous oxide, argon, helium, noble gases, such as xenon, air (nitrogen and oxygen blend), and blends of these materials are preferred because they are easier to use, e.g., fewer environmental and safety concerns. Other suitable physical blowing agents include, e.g., hydrofluorocarbons (HFC), hydrochlorofluorocarbons (HCFC), and fully- or partially fluorinated ethers.

Chemical blowing agents are added to the polymer at a temperature below that of the activation temperature of the blowing agent, and are typically added to the polymer feed at room temperature prior to introduction to the extruder. The blowing agent is then mixed to distribute it throughout the polymer in unactivated form, above the melt temperature of the polypropylene, but below the activation temperature of the chemical blowing agent. Once dispersed, the chemical blowing agent may be activated by heating the mixture to a temperature above the activation temperature of the agent. Activation of the blowing agent liberates gas either through decomposition (e.g., exothermic chemical blowing agents such as azodicarbonamide) or reaction (e.g., endothermic chemical blowing agents such as sodium bicarbonate-citric acid mixtures), such as $N_2$, $CO_2$ and/or $H_2O$, yet cell formation is restrained by the temperature and pressure of the system. Useful chemical blowing agents typically activate at a temperature of 140° C. or above.

Examples of chemical blowing agents include synthetic azo-, carbonate-, and hydrazide based molecules, including azodicarbonamide, azodiisobutyronitrile, benzenesulfonhydrazide, 4,4-oxybenzene sulfonyl-semicarbazide, p-toluene sulfonyl semi-carbazide, barium azodicarboxylate, N,N'-dimethyl-N,N'-dinitrosoterephthalamide and trihydrazino triazine. Specific examples of these materials are Celogen OT (4,4' oxybis(benzenesulfonylhydrazide)). Other chemical blowing agents include endothermic reactive materials such as sodium bicarbonate/citric acid bends that release carbon dioxide. Specific examples include Reedy International Corp SAFOAM products.

With either a chemical or physical blowing agent, as the melt mixture exits the extruder through a shaping die, it is exposed to the much lower atmospheric pressure causing the blowing agent (or its decomposition products) to expand. This causes cell formation resulting in foaming of the melt mixture. When the melt mixture exit temperature is at or below 50° C. above the $T_m$ of the neat polymer, the increase in $T_m$ of the polymer as the blowing agent comes out of the solution causes crystallization of the polypropylene, which in turn arrests the growth and coalescence of the foam cells within seconds or, most typically, a fraction of a second. This preferably results in the formation of small and uniform voids in the polymeric material. When the exit temperature is no more than 50° C. above the $T_m$ of the neat polymer, the extensional viscosity of the polymer increases as the blowing agent comes out of the solution and the polypropylene rapidly crystallizes. When a high melt strength polymer is used, the extensional thickening behavior is especially pronounced. These factors arrest the growth and coalescense of the foam cells within seconds or, most typically, a fraction of a second. Preferably, under these conditions, the formation of small and uniform cells in the polymeric material occurs. When exit temperatures are in excess of 50° C. above the $T_m$ of the neat polymer, cooling of the polymeric material may take longer, resulting in non-uniform, unarrested cell growth. In addition to the increase in $T_m$, adiabatic cooling of the foam may occur as the blowing agent expands.

The amount of blowing agent incorporated into the foamable polymer mixture is generally chosen to yield a foam having a void content in excess of 10%, more preferably in excess of 20%, as measured by density reduction; [1–the ratio of the density of the foam to that of the neat polymer]×100. Generally, greater foam void content reduces the foam density, weight and material costs for subsequent end uses.

Preferably, the formed foam is oriented such as by uniaxial or biaxial stretching in mutually perpendicular directions at a temperature above the alpha transition temperature and below the melting temperature of the polymer matrix (e.g., polypropylene). Generally, in biaxial stretching, the film is stretched in one direction first and then in a second direction perpendicular to the first. However, stretching may be effected in both directions, simultaneously if desired. If biaxial orientation is desired, it is preferable to simultaneously orient the foam, rather than sequentially orient the foam along the two major axes. In a typical sequential orientation process, the film is stretched first in the direction of extrusion over a set of rotating rollers and then stretched in the direction transverse thereto by means of a tenter apparatus. Alternatively, foams may be stretched in both the machine and transverse directions in a tenter apparatus. Foams may be stretched in one or both directions 3 to 75 times total draw ratio (MD×CD) for biaxial stretching or 1-10 times for uniaxial stretching. Generally greater orientation is achievable using foams of small cell size; foams having cell size of greater than 100 microns are not readily biaxially oriented more than 20 times, while foams having a cell size of 50 microns or less could be stretched up to 75 times total draw ratio. In addition foams with small average cell size exhibit greater tensile strength and elongation to break after stretching.

The final thickness of the foam will be determined in part by the extrusion thickness, the degree of orientation, and any additional processing. The present invention provides thinner foams than are generally achievable by prior art processes. Most foams are limited in thickness by the cell size. In the present invention, the small cell sizes (100 microns or less) in combination with the orientation allows a foam sheet thickness of 25 microns to 1000 microns, and foam sheets of 25 microns to 100 microns are readily prepared. This is extremely desirable with microstructured hook structures as a soft conformable backing is obtained that can be used in many uses where contact with an active wearer (e.g., a person) is desired or possible. Specifically, the foamed hook with microstructured hooks can be used with disposable absorbent articles such as diapers as a closure tab, which is soft to the touch and is aesthetically pleasing due to its pearlescent appearance. Other uses where a hook strip or tab would be in contact with a sensitive surface would include medical wrap, sport wraps, headbands, produce wraps and feminine hygiene articles. Suitable backings can have a softness of from 10 to 2000 Gurley units, preferably from 10 to 200 Gurley units.

Preferably, the foam can have cell sizes of 2 to 100 microns, preferably 5 to 50 microns. The foam may alternatively, or additionally, have a cell size distribution with a polydispersity from 1.0 to 2.0, preferably from 1.0 to 1.5, more preferably from 1.0 to 1.2.

The polymer foam surface microstructures generally have at least one cross-sectional extent of about 10 microns or more, preferably 50 microns or more, and if a discrete microstructure rather than a continuous or discontinuous rib or the like the microstructure could have a maximum extent of about 300 microns or less, preferably 200 microns or less, a maximum height of 1000 microns or less, preferably 750 microns or less and a minimum height of 200 microns or more, preferably 300 microns or more. An extent of the microstructure is generally considered a dimension of the microstructure from one face to an opposite or opposing face or interface (e.g. the base of the microstructure where it is joined to the backing) and could be a width, a height or a thickness dimension or some other dimension at some portion of the microstructure.

The microstructures smallest cross-sectional dimension is generally 10 microns or more. The smallest cross-sectional dimension generally would exclude the tips of a microstructure, and would generally be measured at a distance of 10 microns or more from a tip. The smallest cross-sectional dimension could generally be any extent such as a length, width or height dimension or any other extent that would be the shortest distance that could be drawn from one surface or face of the microstructure to an opposing surface or face. The microstructure height is generally 1000 microns or less, preferably 750 microns or less. The ratio of the mean foam cell size to the smallest cross-sectional dimension is 0.75 or less, preferably 0.5 or less. The foamed article may be provided in a variety of shapes, including a rod, a cylinder, a sheet, etc. Preferably, the foam is provided in the form of a sheet, the foam has a pair of major surfaces, one or both of which can be provided with surface microstructures. The foam backing and microstructures both include a plurality of voids, which voids are of a mean size substantially less than the smallest cross-sectional dimension or extent of the microstructures.

The foam can also comprise at least one layer in a multi-layer construction by a coextrusion process whereby a foam is coextruded with at least one other material, which may be a foamed or unfoamed material. For example, the foam can comprise some or all of the surface microstructures with a non-foamed backing or, conversely, the foam can comprise some or all of the backing with non-foamed surface microstructures.

The coextrusion process may be used to make a foam material comprising two layers or more. A layered material or article may be produced by equipping a die with an appropriate feed block, e.g., a multilayer feedblock, or by using a multi-vaned or multi-manifold die such as a 3-layer vane die available from Cloeren Corp. (Orange, Tex.). Materials or articles having multiple adjacent foam layers may be made with foam layers comprising the same or different materials. Foam articles of the present invention may comprise one or more interior and/or exterior foam layer(s). In such a case, each extrudable, foamable material may be processed using one of the above-described extrusion methods wherein melt mixtures are fed to different inlets on a multi-layer feedblock, or multi-manifold die, and are brought together prior to exiting the die. The layers foam in generally the same manner as described above for the extrusion process. The multi-layer process can also be used to extrude the foam of this invention with other types of materials such as unfoamed polymeric materials and any other type of polymeric material. When a multi-layered article is produced, it is preferable to form adjacent layers using materials having similar viscosities and which provide interlayer adhesion.

If adjacent layers of materials are heated to substantially different temperatures, a die can be used that will thermally isolate the different materials until just prior to their exiting the die, for example the die disclosed in U.S. Pat. No. 5,599,602. This can diminish or eliminate negative effects of contacting the different materials such as melting or collapsing the foam or causing continued cell expansion coalescense.

The foamable melt mix may also include additives. Examples of suitable additives include tackifiers (e.g., rosin esters, terpenes, phenols, and aliphatic, aromatic, or mixtures of aliphatic and aromatic synthetic hydrocarbon resins), plasticizers (other than physical blowing agents), nucleating agents (e.g., talc, silicon, or $TiO_2$), pigments, dyes, reinforcing agents, solid fillers, hydrophobic or hydrophilic silica, calcium carbonate, toughening agents, flame retardants, antioxidants, finely ground polymeric particles (e.g., polyester, nylon, or polypropylene), glass beads, stabilizers (e.g., UV stabilizers), and combinations thereof.

A preferred microstructure formed in the present invention is a microstructured hook. A first method of forming foamed microstructured hook strips with a continuous foam film-like film backing is by extruding a foamable semi-crystalline thermoplastic resin through a die onto a continuously moving mold surface with cavities. This is generally a roll surface 3 as shown in FIG. 1. The molten foam is extruded or forced into the cavities 12 by pressure generally by use of a nip. In the case of FIG. 1, the nip is formed by the extruder die 8 and the roll 3 but alternatively the polymer could be extruded between two roll surfaces or the like. The nip or gap is sufficient that a film backing 30 is also formed over the cavities. The film backing preferably has a smooth surface along the back but could have a textured or rough surface. The formed material 20 has projection or hook elements 28 projecting from a foam backing 30 which material is removed from the mold surface by a take-up device 2. A vacuum can be used to evacuate the cavities for easier extrusion into the cavities.

Figure 2:
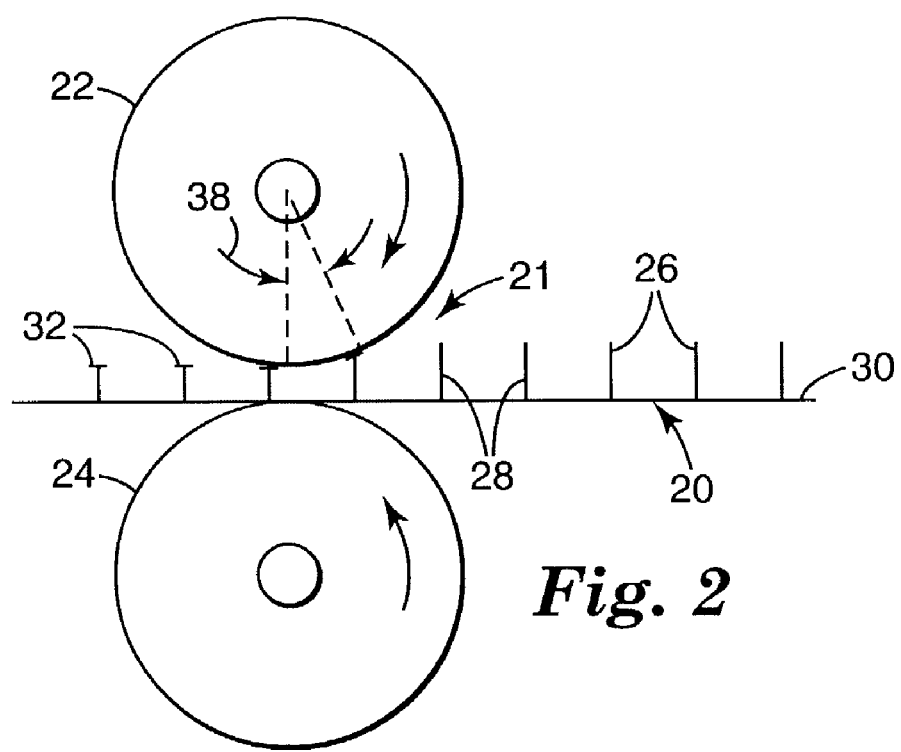
FIG. 2 is a schematic view of a further method used in forming hook strip in accordance with the present invention.

The cavities 12 could be in the shape of the final hook elements as disclosed, for example, in U.S. Pat. Nos. 6,174,476 or 6,540,497. In this case, a generally continuously tapered hook is pulled from continuously tapered hook cavities in its final hook form or at least a partially formed hook element. Also, the extruded strip 20 could be a foam web provided with only partially formed hook elements or, as shown in FIG. 2, unformed hook elements forming projections. The tip portion 26 of these projections (or the tips of partially formed hook elements) then could be subsequently formed into the desired finished hook elements 32. This would, in a preferred method, be done by deforming the tip portions using heat and/or pressure. The heat and pressure, if both are used, could be applied sequentially or simultaneously. In a preferred method, heat and pressure is selectively applied to the tip portion 26 in a nip 21. In this case, there is provided a nip 21 having at least one first heated surface member 22 and at least one second opposing surface member 24. The nip has a gap which gap has a compression zone defined by a first entry gap width and a second end gap width. The first gap width is substantially equal to or less than the web first average thickness. The second end gap width is less than the first web thickness and is the smallest gap width of the nip 21. The final hook strip has formed hook heads 32 on the projection 28.

A specific suitable method for forming a foam having an array of upstanding projections for use in the FIG. 2 process is shown in FIG. 1. A feed stream of preselected foamable thermoplastic resin is fed by conventional means into an extruder 6 which melts the resin and moves the heated resin to a die 8. The die 8 extrudes the resin as a wide ribbon of material onto a mold surface 3, e.g., a cylinder, having an array of mold cavities 12 in the form of elongated holes, which preferably taper to facilitate removal of the solidified resin from the mold cavities. These holes or mold cavities are preferably in the form of straight (i.e., only one axis in the length direction) cavities. The mold cavities can be connected to a vacuum system (not shown) to facilitate resin flow into the mold cavities. This could require a doctor blade or knife to remove excess material extruded into the interior face of the mold cylinder. The mold cavities 12 preferably terminate in the mold surface having an open end for entry of the liquid resin and a closed end. In this case, a vacuum could be used to at least partially evacuate the mold cavities 12 prior to entering the die 8. The mold surface 3 preferably matches that of the die 8 where they are in contact to prevent excess resin being extruded out, e.g., the die side edges. The mold surface and cavities can be air or water cooled, or the like, prior to stripping the integrally formed backing and upstanding formed stems from the mold surface such as by a stripper roll 2. This provides a web 20 of a backing 30 having integrally formed upstanding stems or hooks 28 of thermoplastic material. Alternatively, upstanding stems could be formed on a preformed backing or the like by extrusion molding or other known techniques.

More specifically describing the FIG. 2 process, the heated calender roll 22 contacts a predetermined portion of a distal end 26 of the stems 28 projecting upward from the backing 30 to form a capped head 32. The roll temperature will be that which will readily deform the distal ends 26 under pressure created by the nips in the compression zone 38 without causing resin to stick to the roll 22 surface. The roll 22 surface can be treated with release coatings resistant to high temperature to allow for higher temperatures and/or longer contact times between the stem tips or distal ends 26 and the heated roll 22.

The hooks are generally of uniform height, preferably from about 0.10 to 1.3 mm in height, and more preferably from about 0.2 to 0.5 mm in height. The capped stem hooks have a density on the backing preferably of from 60 to 1,600 hooks per square centimeter, and in one preferred embodiment from about 100 to 700 hooks per square centimeter. With capped hooks, the stem portions have a diameter adjacent the heads of preferably from 0.07 to 0.7 mm, and more preferably from about 0.1 to 0.3 mm. The capped heads project radially past the stem base portions on at least one side, preferably two or more sides, preferably by, on average, about 0.01 to 0.3 mm, and more preferably by, on average, about 0.02 to 0.25 mm and have average thicknesses between their outer and inner surfaces (i.e., measured in a direction parallel to the axis of the stems) preferably from about 0.01 to 0.3 mm and more preferably from about 0.02 to 0.1 mm. The capped heads have an average diameter (i.e., measured radially of the axis of the capped heads and the stems) to average capped head thickness ratio preferably from 1.5:1 to 12:1, and more preferably from 2.5:1 to 6:1.

For most hook-and-loop uses, the hooks should be distributed substantially uniformly over the entire surface area of the hook strip, usually in a square, staggered or hexagonal array. For hermaphroditic uses, the hooks preferably are distributed to prevent lateral slippage when engaged.

Figure 3:
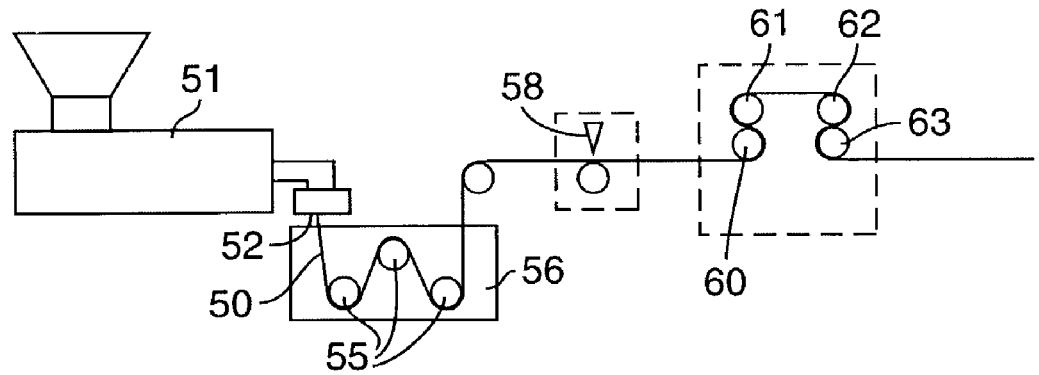
FIG. 3 is a schematic view of a second method for forming an extruded hook strip in accordance with the invention.
Figure 4:
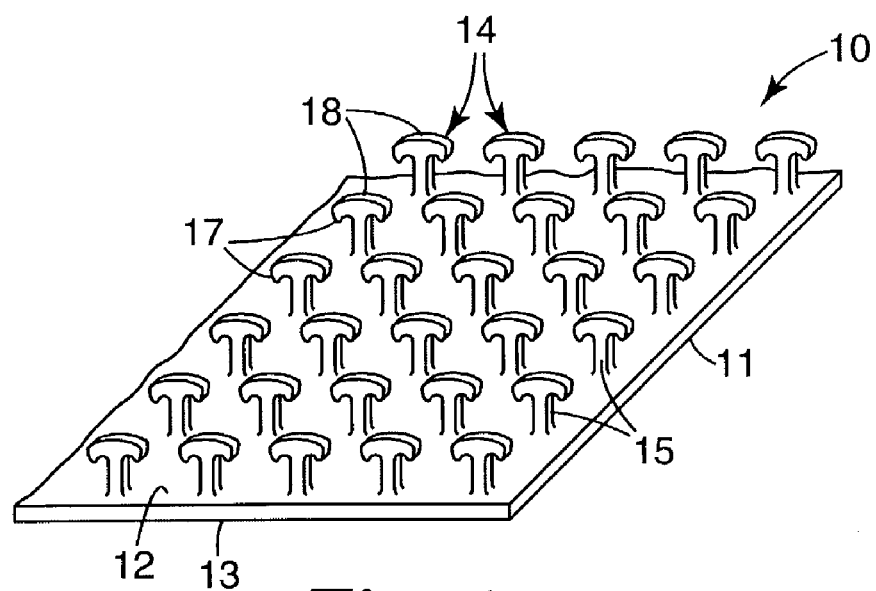
FIG. 4 is an enlarged perspective view of a hook fastener formed by the method of FIG. 3.

A second method for forming a foamed hook strip having hooks, such as that of FIG. 4, is schematically illustrated in FIG. 3. Generally, the method includes first extruding a strip 50 of foamable thermoplastic resin from an extruder 51 through a die 52 having an opening cut, for example, by electron discharge machining, shaped to form the strip 50 with a base and elongate spaced ribs projecting above an upper surface of the base layer that have the cross sectional shape of the hook portions or members to be formed. The foamed strip 50 is pulled around rollers 55 through a quench tank 56 filled with a cooling liquid (e.g., water), after which the ribs (but not the base layer) are transversely slit or cut at spaced locations along their lengths by a cutter 58 to form discrete portions of the ribs having lengths corresponding to about the desired thicknesses of the hook portions to be formed. Optionally, the strip can be stretched prior to cutting to provide further molecular orientation to the polymers forming the ribs and/or reduce the size of the ribs and the resulting hook members formed by slitting of the ribs. The cutter 58 can cut using any conventional means such as reciprocating or rotating blades, lasers, or water jets, however preferably it cuts using blades oriented at an angle of about 60 to 80 degrees with respect to length of the ribs.

After cutting of the ribs, the base of the strip 50 is longitudinally stretched at a stretch ratio of at least 2 to 1, and preferably at a stretch ratio of about 4 to 1, preferably between a first pair of nip rollers 60 and 61 and a second pair of nip rollers 62 and 63 driven at different surface speeds. Optionally, the strip 50 can also be transversely stretched to provide biaxial orientation to the base. Roller 61 is preferably heated to heat the base prior to stretching, and the roller 62 is preferably chilled to stabilize the stretched base. Stretching causes spaces between the cut portions of the ribs, which then become the hook portions or members 74 for the completed hook fastener portion 70.

Figure 5:
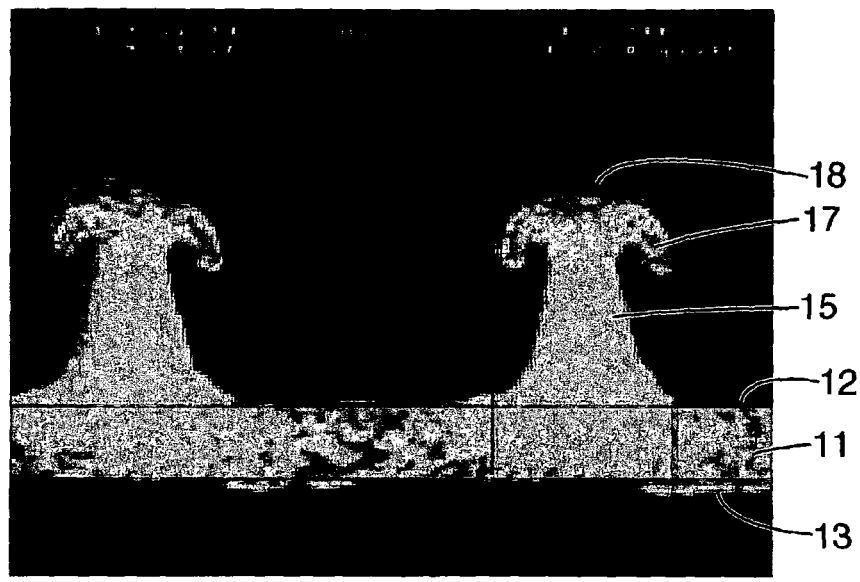
FIG. 5 is a cross-section photomicrograph of a foamed hook formed by a method such as shown in FIGS. 1 and 2.
Figure 6:
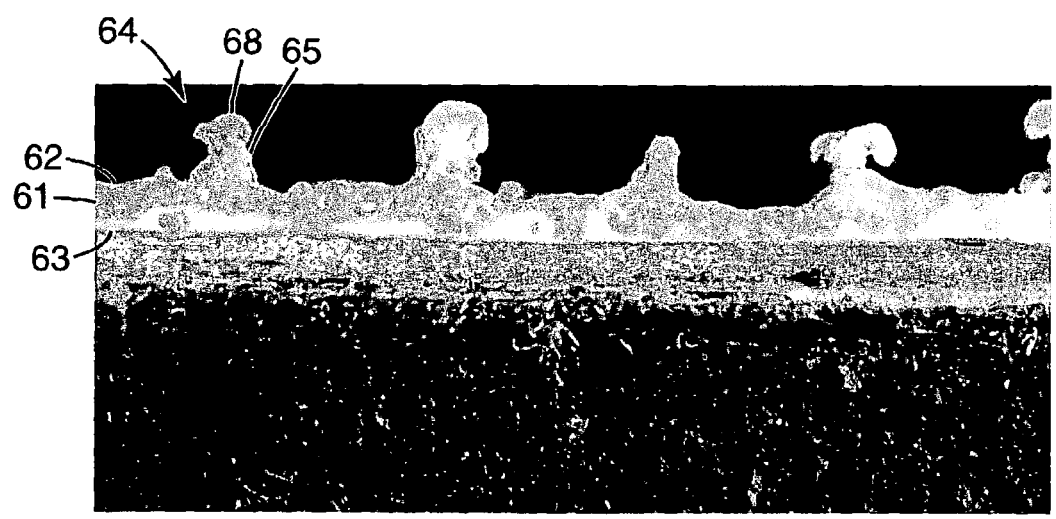
FIG. 6 is a counterexample photomicrograph of a foamed hook formed by a method in FIGS. 1 and 2.
Figure 7:
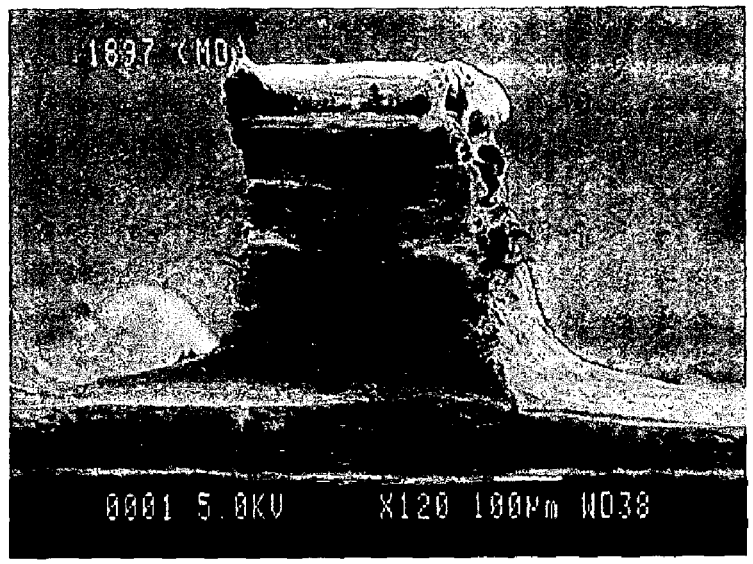
FIG. 7 is a photomicrograph of a foamed hook formed by a method such as shown in FIG. 3.
Figure 8:
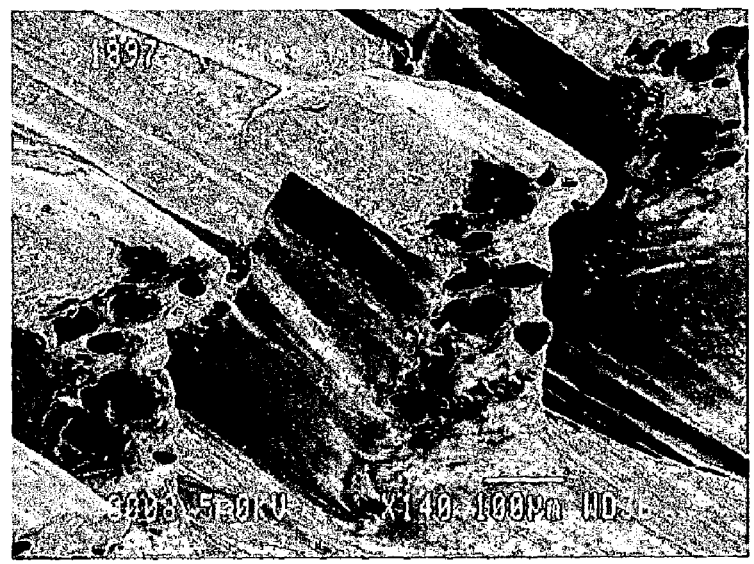
FIG. 8 is a photomicrograph of a foamed hook formed by a method such as shown in FIG. 3.

Referring now to FIGS. 4 and 5, a hook fastener portion 10 comprises a thin strong flexible film-like foamed backing 11 having generally parallel upper and lower major surfaces 12 and 13, and a multiplicity of spaced hook members 14 projecting from at least the upper surface 12 of the backing 11. The backing can have planar surfaces or surface features as could be desired for tear resistance or reinforcement. The hook members 14 each comprise a stem portion 15 attached at one end to the backing 11 and preferably having tapered sections that widen toward the backing 11 to increase the hook anchorage and breaking strengths at their junctures with the backing 11, and a head portion 17 at the end of the stem portion 15 opposite the backing 11. The sides of the head portion 17 can be flush with the sides of the stem portion 15 on two opposite sides. The head portion 17 has hook engaging parts or arms projecting past the stem portion 15 on one or both sides. The hook member has a rounded surface 18 opposite the stem portion 15 to help the head portion 17 enter between loops in a loop fastener portion. The head portion 17 also has transverse cylindrically concave surface portions at the junctures between the stem portion 15 and the surfaces of the head portion 17 projecting over the backing 11. The foam cell size is substantially smaller than the smallest cross-sectional extent of the microstructural hook element. FIG. 6 is an embodiment of a hook fastener portion 64 formed with a foam having a cell size range that is larger than the smallest cross-sectional extent of the hook members 65. The hook heads 68 are misformed or nonexistent. The backing 61 is irregular and its upper and lower surfaces 62 and 63 are nonparallel and has significant variations in thickness.

In certain applications, it has been discovered that very low hook densities are desirable. For example, hook densities of less than 100, preferably less than 70 and even less than 50 hook per square centimeter are desirable when used to attach to low loft nonwovens using a relatively large area flexible hook fastener tab or patch formed of a foamed hook fastener. This low spacing has been found to increase the hooking efficiency of the individual hook element, particularly relative to low cost and otherwise ineffective nonwoven materials not traditionally used as loop products. The hook tab or patch is also made flexible by suitable selection of the polymer forming the base layer and/or by the stretching of the foam base layer reducing its thickness, to a preferred range of 100 μm to 25 μm. Biaxial orientation also reduces the hook density to the desired range for a large area hook fastener.

A large area fastener when used on a garment type application such as diapers or the like provides stability between the two engaged regions. A suitable large area fastener would have a surface area of 5 to 100 cm$^2$, preferably 20 to 70 cm$^2$.

When a large area (oversized) fastener is brought forward or backward for engagement with an outer surface of an article, the oversized fastener may be capable of fastening into any portion of the outer surface of the article. With this, the need for a specific attachment region or target attachment zone can be eliminated if the garment can engage at some minimum level with the fastener. The larger area also ensures secure closure due to the fasteners size. As such, large area foamed hook fasteners of the invention could potentially eliminate the need for a separate loop component or other "mating" fastener component on the breathable backing of the garment or article. The increased size of the large area fastener also can eliminate the need for secondary fasteners or bonded areas (such as passive bonds) that may be required to stabilize the overlapped regions of the article or garment.

Use of large area fastener reduces the manufacturing complexity of a garment such as an absorbent article by eliminating the need for additional bond points or multiple fasteners to stabilize the fastening system of e.g., the front and rear waist regions. The addition of bond points or additional fasteners increases the complexity of the manufacturing process.

Specifically, a large area hook fastener, is capable of directly engaging an outer surface of a diaper provided with a relatively low loft nonwoven without the need for an expensive loop patch. The large area flexible hook fastener can also prevent inadvertent opening of the closure due to the large contact and attachment area creating a more stable garment closure. The oversized hook fastener could also be used in a prefastened pull-on type garment, due to its large area of large area contact, making the garment suitably stable for packaging and subsequent use.

Figure 9:
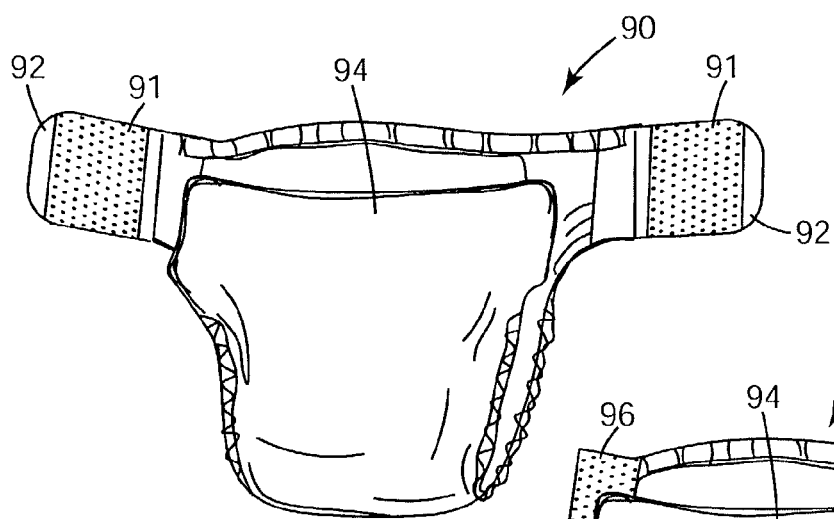
FIG. 9 is a perspective view of a disposable garment using a breathable hook fastener member according to the present invention.
Figure 10:
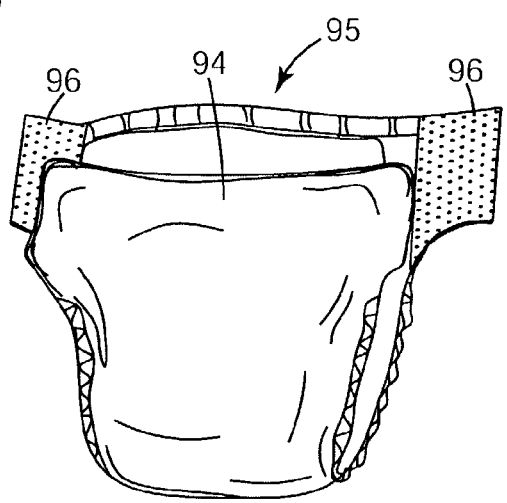
FIG. 10 is a perspective view of a disposable garment using a hook member according to the present invention.
Figure 11:
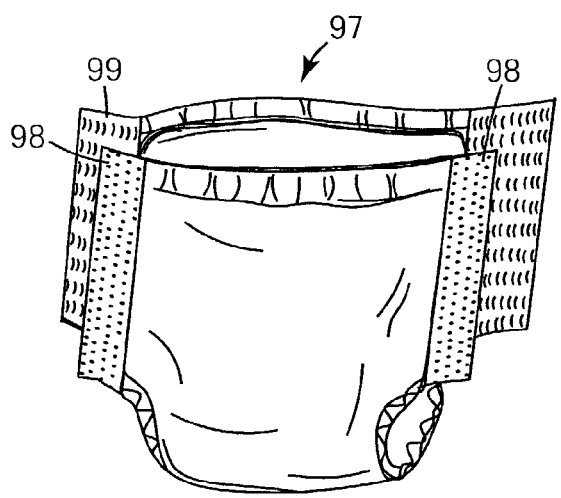
FIG. 11 is a perspective view of a disposable garment using a hook member according to the present invention.
Figure 12:
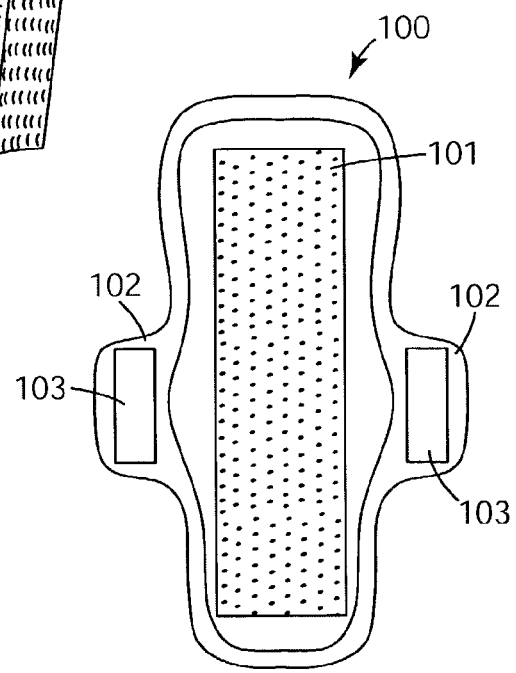
FIG. 12 is a perspective view of a feminine hygiene article using a hook member according to the present invention.

Examples of suitable uses for this low hook density large area hook fastener element, as a hook tab or patch, are illustrated in FIGS. 9-12, 14 and 15. In FIG. 9, a large area foam fastening tab is attached to a breathable carrier substrate 92 such as a nonwoven web, which is attached to a diaper 90 as is known in the art. The fastening tab could be of a size of from 5 to 100 cm$^2$, preferably 20 to 70 cm$^2$ and can be attached directly to a low loft nonwoven 94 forming the outer cover of the diaper 90. Typically, this low loft nonwoven would be a spunbond web, a bonded carded or air laid web, a spunlace web or the like. FIG. 10 is a variation of this fastening tab type construction for a diaper 95, however, where the hook tab 96 is directly bonded to the diaper 95, either at an ear cutout portion or at the edge region of the diaper. FIG. 11 is a further embodiment of a large area hook tab 98 used with a pull up type diaper design 97. In this embodiment, the hook tab 98 would engage a suitable mating region 99 on the opposite face of the pull up diaper. Of course, these two elements could be reversed. In both cases, the mating region could be a nonwoven used to form the nonwoven outer cover of the diaper or the nonwoven fluid permeable topsheet. FIG. 12 is an embodiment of the invention hook material being used as a large area patch 101 on a feminine hygiene article 100. The patch could be used as the primary attachment element to the undergarment, optionally a secondary attachment element 103 could be provided on attachment wings 102. The use of the low hook density element as a large area patch could also be used on a diaper where the patch could form a part or all of the diaper outer cover.

Figure 13:
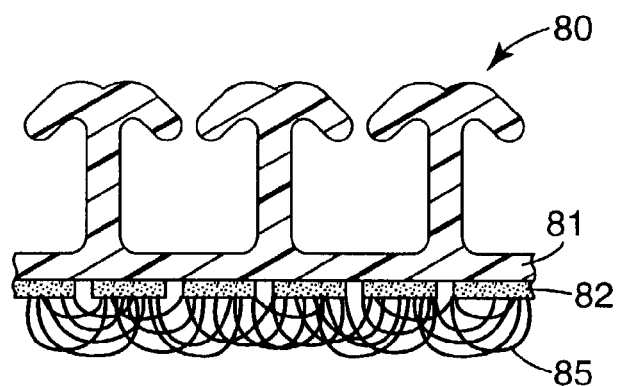
FIG. 13 is a breathable hook fastener of the present invention as a self-engaging structure.

FIG. 13 is an example of the large area fastener 80 provided with a loop material 85 on the face opposite that having the hook elements. The loop is a woven or nonwoven type loop and can be applied to the backing 81 of the large area hook fastener 80 by bonding 82 which can be adhesive, heat, pressure or sonic bonding combinations thereof.

Figure 14:
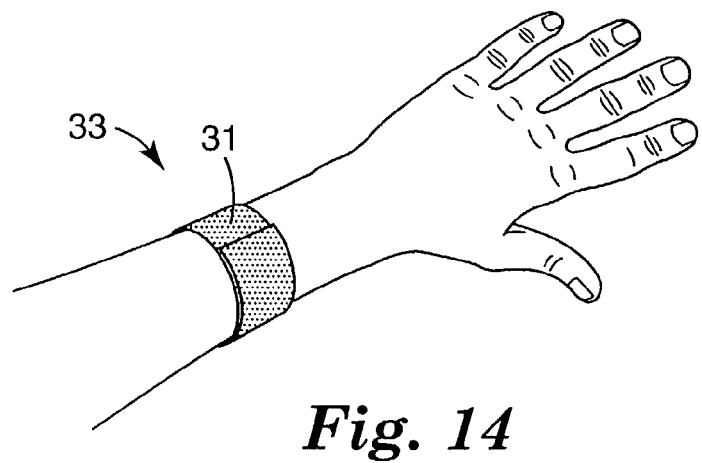
FIG. 14 is a breathable hook fastener of the present invention used as a body wrap.
Figure 15:
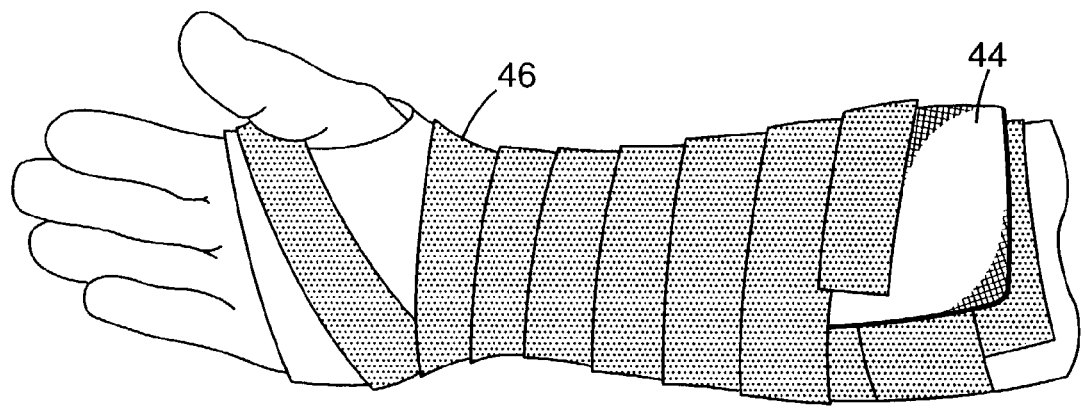
FIG. 15 is a breathable hook fastener of the present invention used as a body wrap.

This type of self-engaging fasteners 31 can be used as a wrap 33 such as shown in FIG. 14, for use as a sport wrap. The self-engaging fastener can also be used as a wrap for articles such as produce, where softness would be beneficial. FIG. 15 shows the self-engaging fastener 46 as a medical wrap which could be used with an absorbent pad 44, if desired, or use of the absorbent pad could be optional if the loop fabric was absorbent.

Test Methods

135 Degree Peel Test

The 135 degree peel test was used to measure the amount of force that was required to peel a sample of the mechanical fastener hook material from a sample of loop fastener material. A 5.1 cm×12.7 cm piece of a loop test material was securely placed on a 5.1 cm×12.7 cm steel panel by using a double-coated adhesive tape. The loop material was placed onto the panel with the cross direction of the loop material parallel to the long dimension of the panel. A 1.9 cm×2.5 cm strip of the mechanical fastener to be tested was cut with the long dimension being in the machine direction of the web. A 2.5 cm wide paper leader was attached to the smooth side of one end of the hook strip. The hook strip was then centrally placed on the loop so that there was a 1.9 cm×2.5 cm contact area between the strip and the loop material and the leading edge of the strip was along the length of the panel. The strip and loop material laminate was then rolled by hand, twice in each direction, using a 1000 gram roller at a rate of approximately 30.5 cm per minute. The sample was then placed in a 135 degree peel jig. The jig was placed into the bottom jaw of an Instron™ Model 1122 tensile tester. The loose end of the paper leader was placed in the upper jaw of the tensile tester. A crosshead speed of 30.5 cm per minute and a chart recorder set at a chart speed of 50.8 cm per minute was used to record the peel force as the hook strip was peeled from the loop material at a constant angle of 135 degrees. An average of the four highest peaks was recorded in grams. The force required to remove the mechanical fastener strip from the loop material was reported in grams/2.54 cm-width. A minimum of 10 tests were run and averaged for each hook and loop combination.

Loop material 'A' was used to measure the performance of the mechanical fastener hook materials. Loop material 'A' is a nonwoven loop made similar to that described in U.S. Pat. No. 5,616,394 Example 1, available from the 3M Company as KN-1971. The loop test material was obtained from a supply roll of the material after unwinding and discarding several revolutions to expose "fresh" material. The loop test material thus obtained was in a relatively compressed state and was used immediately in the peel test before any significant relofting of the loops could occur.

135 Degree Twist Peel Test

A 135 degree twist peel test was used to measure the amount of force that was required to peel a sample of the mechanical fastener hook material from a sample of low profile loop fastener material. A 1.9 cm×2.5 cm strip of the mechanical fastener to be tested was cut with the long dimension being in the machine direction of the web. A 2.5 cm wide paper leader was attached to the smooth side of one end of the hook strip. The hook materials were fastened to the low profile loop material using the following procedure: The hook material, with hook side down, was placed onto the low profile loop backsheet material of a diaper. A 4.1 kg weight measuring 7.6 cm×7.6 cm with medium grit abrasive paper on the bottom surface, was placed on top of the hook material. To engage the hook with the backsheet loop material, the diaper was held securely flat and the weight was twisted 45 degrees to the right, then 90 degrees to the left, then 90 degrees right and then 45 degrees left. The weight was then removed and the diaper was held firm against the surface of a 135 degree jig stand mounted into the lower jaw of an Instron™ Model 1122 tensile tester. The loose end of the paper leader attached to the hook material was placed in the upper jaw of the tensile tester. A crosshead speed of 30.5 cm per minute and a chart recorder set at a chart speed of 50.8 cm per minute was used to record the peel force as the hook strip was peeled from the loop material at a constant angle of 135 degrees. An average of the four highest force peaks was recorded in grams and was reported in grams/2.54 cm-width. 10 different locations were tested on each diaper with the average of the 10 being reported in Table 4.

Loop material 'B' was used to measure the performance of the mechanical fastener hook material. Loop material 'B' is the nonwoven side (i.e. outward facing side) of the backsheet of a Loving Touch diaper size 3.

Density and Void Content

Density of the webs was measured using ASTM D792-86. The amount of blowing agent incorporated into the foamable polymer mixture is generally chosen to yield a foam having a void content in excess of 10%, more preferably in excess of 20%, as measured by density reduction; [1−the ratio of the density of the foam to that of the neat polymer]×100. Generally, greater foam void content reduces the foam density, weight and material costs for subsequent end uses.

Stiffness

The conformability or stiffness of the webs was measured using the Gurley Stiffness test as described in ASTM T543.

Opacity

The opacity of the webs was measured using ASTM D1746.

Cell Size and Polydispersity of Cell Size Distribution

A Leica microscope equipped with a zoom lens at a magnification of approximately 25× was used to take an optical micrograph of a cross-section of the foam. The sizes of 20 cells were measured and weight average and number average size was determined. The ratio of the weight average size to their number average size is reported as the polydispersity of cell size distribution.

Hook Dimensions

The dimensions of the Example and Comparative Example hook materials were measured using a Leica microscope equipped with a zoom lens at a magnification of approximately 25×. The samples were placed on a x-y moveable stage and measured via stage movement to the nearest micron. A minimum of 3 replicates were used and averaged for each dimension. The base film thickness and hook rail height was measured both before and after the orientation step.

EXAMPLE 1

A mechanical fastener hook web was made using apparatus similar to that shown in FIG. 1. A blend of 49% polypropylene/polyethylene impact copolymer (7C06, 1.5 MFI, Dow Chemical Corp., Midland, Mich.), 49% high melt strength polypropylene homopolymer (FH3400, Chisso Corp. Tokyo, Japan) and 2% chemical blowing agent concentrate (FM1307H, 50% azodicarbonamide/50% LDPE, Ampacet Corp., Tarrytown, N.Y.) was extruded with a 6.35 cm single screw extruder (24:1 L/D) using a "humped" barrel temperature profile of 135° C.-216° C.-177° C. and a die temperature of approximately 204° C. Decomposition of the blowing agent into gaseous nitrogen occurred in the second zone of the extruder. The extrudate was extruded vertically downward through a die equipped with a die lip having an opening cut by electron discharge machining. After being shaped by the die lip, the extrudate was quenched in a water tank at a speed of 10.4 meter/min with the water being maintained at approximately 16° C.-20° C. The resulting structure was foamed in its entirety, i.e. both the base film layer and the upstanding hook rails were foamed. The web was then advanced through a cutting station where the ribs (but not the base layer) were transversely cut at an angle of 23 degrees measured from the transverse direction of the web. The spacing of the cuts was 254 microns. After cutting the ribs, the base of the web was longitudinally stretched at a stretch ratio of approximately 3.5 to 1 between a first pair of nip rolls and a second pair of nip rolls to further separate the individual hook elements to approximately 8 hooks/cm. The upper roll of the first pair of nip rolls was heated to 143° C. to soften the web prior to stretching. There were approximately 10 rows of ribs or cut hooks per centimeter. The base film layer had a thickness of approximately 230 microns. The width of the individual hook elements was approximately 520-570 microns as measured in the cross-direction of the web. The mean cell size of the foam cells was 53 microns with a polydispersity index of 1.08. The cross-section of the web is shown in FIG. 5.

EXAMPLE 2

A mechanical fastener hook web was made as in Example 1 except only the base film layer was foamed. A blend of 49% polypropylene/polyethylene impact copolymer (C104, 1.5 MFI, Dow Chemical), 49% high melt strength polypropylene homopolymer (FH3400) and 2% chemical blowing agent concentrate (FM1307H) was extruded with a 6.35 cm single screw extruder (24:1 L/D) using a "humped" barrel temperature profile of 135° C.-210° C.-177° C. and a die temperature of approximately 204° C. to form the base film layer. 100% C104 copolymer was used to form the non-foamed hook rails and was extruded with a 3.8 cm single screw extruder (28:1 L/D) using a sloped barrel profile of 204° C. in the feed zone to 232° C. in the last zone. The melt streams of the two extruders were fed to a three layer coextrusion feedblock (Cloeren Co., Orange, Tex.) with the third layer inlet blocked such that a two layer output resulted. The feedblock was mounted onto a 20 cm die equipped with the same profiled die lip as in Example 1. The feedblock and die were maintained at 204° C. After being shaped by the die lip, the extrudate was quenched in a water tank at a speed of 10.7 meter/min with the water being maintained at approximately 16° C.-20° C. The web was then advanced through a cutting station where the ribs (but not the base layer) were transversely cut at an angle of 23 degrees measured from the transverse direction of the web. The spacing of the cuts was 254 microns. After cutting the ribs, the base of the web was longitudinally stretched at a stretch ratio of approximately 3.5 to 1 between a first pair of nip rolls and a second pair of nip rolls to further separate the individual hook elements to approximately 8 hooks/cm. The upper roll of the first pair of nip rolls was heated to 143° C. to soften the web prior to stretching. There were approximately 10 rows of ribs or cut hooks per centimeter. The base film layer had a thickness of approximately 240 microns. The width of the individual hook elements was approximately 305-356 microns as measured in the cross-direction of the web. The mean cell size of the foam cells was 61 microns with a polydispersity index of 1.05.

EXAMPLE 3

A mechanical fastener hook web was made as in Example 2 except the hook rails were foamed and the base film layer was unfoamed. A blend of 49% C104 copolymer, 49% FH3400 polypropylene and 2% chemical blowing agent concentrate (FM1307H) was extruded with a 3.8 cm single screw extruder (28:1 L/D) using a "humped" barrel temperature profile of 135° C.-210° C.-177° C. to form the hook rails. 100% 7C06 impact copolymer (Union Carbide Corp., Danbury, Conn.) was used to form the non-foamed base film layer and was extruded with a 6.35 cm single screw extruder (24:1 L/D) using a sloped barrel profile of 204° C. in the feed zone to 232° C. in the last zone. The melt streams of the two extruders were fed to a three layer coextrusion feedblock (Cloeren Co., Orange, Tex.) with the third layer inlet blocked such that a two layer output resulted. The feedblock was mounted onto a 20 cm die equipped with a profiled die lip. The feedblock and die were maintained at 204° C. After being shaped by the die lip, the extrudate was quenched in a water tank at a speed of 4.6 meter/min with the water being maintained at approximately 16° C.-20° C. The resulting structure had a non-foamed base film layer with upstanding hook rails that were foamed approximately 70% of their height as measured from the top downward towards the base. The web was then advanced through a cutting station where the ribs (but not the base layer) were transversely cut at an angle of 23 degrees measured from the transverse direction of the web. The spacing of the cuts was 305 microns. After cutting the ribs, the base of the web was longitudinally stretched at a stretch ratio of approximately 3.5 to 1 between a first pair of nip rolls and a second pair of nip rolls to further separate the individual hook elements to approximately 12 hooks/cm. The upper roll of the first pair of nip rolls was heated to 143° C. to soften the web prior to stretching. There were approximately 15 rows of ribs or cut hooks per centimeter. The base film layer had a thickness of approximately 165-240 microns. The width of the individual hook elements was approximately 200 microns as measured in the cross-direction of the web. The mean cell size of the foam cells was 50 microns with a polydispersity index of 1.03.

EXAMPLE 4

A mechanical fastener hook web was made using the microreplicated molding process described in U.S. Pat. No. 5,845,375 and apparatus similar to that shown in FIG. 1. A blend of 29% ultra low density polyethylene (AFFINITY 8200, Dow Chemical Corp.), 68% high melt strength polypropylene homopolymer (PROFAX PF814, Basell USA) and 2% FM1307H chemical blowing agent concentrate was extruded with a 6.35 cm single screw extruder (24:1 L/D) using a "humped" barrel temperature profile of 143° C.-232° C.-154° C. and a die temperature of approximately 163° C. Decomposition of the blowing agent into gaseous nitrogen occurred in the second zone of the extruder. The extrudate was extruded vertically downward at a linespeed of 4.3 meter/min into a nip formed by a silicone rubber covered roll and a steel roll. Nip pressure was controlled to 1.1 kg/cm$^2$ (15 psi) and the temperatures of both rolls were maintained at 32° C. The silicone rubber covering of the rubber roll was machined to have cavities approximately 2300 microns in depth at a roll surface density of approximately 46 cavities per square centimeter using the process described in U.S. Pat. No. 5,792,411. The mean cell size of the foam cells was 58 microns with a polydispersity index of 1.07. The small cell sizes of the foamed melt allowed for accurate replication of the cavities in the silicone rubber resulting in a foamed base film of approximately 1020 microns in thickness having discrete upstanding foamed projections approximately 760 microns in height.

Comparative Example C1

A mechanical fastener hook web was made similar to Example 1 except no high melt strength polypropylene was used in the blended extrudate which consisted of 98% 7C06 copolymer and 2% FM1307H blowing agent. The absence of the high melt strength polypropylene resulted in significantly larger foam cell sizes in the extrudate and as a result, replication of the die lip profile was very poor with significant feature distortions. An optical photograph of a cross-section of the web is shown in FIG. 6.

Table 1 below shows some of the dimensions and properties of the webs prior to the cutting and orientation step.

TABLE 1

| Example | Density (g/cm³) | Void Content (%) | Base Thickness (μm) | Hook Rail Height (μm) |
|---|---|---|---|---|
| 1 | 0.518 | 40 | 229 | 592 |
| 2 | 0.603 | 32.5 | 241 | 442 |
| 3 | | 10 | 203 | 546 |

Table 2 below shows some of the dimensions and properties of the webs after the cutting and orientation step.

TABLE 2

| Example | Density (g/cm³) | Base Thickness (μm) | Hook Rail Height (μm) | Hook Thickness (μm) |
|---|---|---|---|---|
| 1 | 0.444 | 109 | 541 | 254 |
| 2 | 0.442 | 97 | 648 | 254 |
| 3 | | 74 | 439 | 305 |

Table 3 below shows some additional properties of the hook materials.

TABLE 3

| Example | 135 Peel Strength (g/cm) | 135 Twist Peel Strength (g/cm) | Gurley Stiffness (mg) | Opacity (%) |
|---|---|---|---|---|
| 1 | | 43 | 16 | 49.6 |
| 2 | | | 10 | |
| 3 | 44 | 45 | | |

We claim:

1. An article comprising a base layer made of thermoplastic polymer having at least one outer face, said outer face containing over at least one area a plurality of foamed hook shaped microstructures comprised of multiple discrete foam cells, the foamed hook shaped microstructures comprising a semicrystalline thermoplastic polymer, the foamed hook shaped microstructures having at least one dimension which is greater than 10 microns and the discrete foam cells forming the foamed hook shaped microstructures having a mean cell size less than the smallest cross-sectional dimension of the foamed hook shaped microstructures excluding any tips on the foamed hook shaped microstructures and measured at a distance of at least 10 microns from such tips, wherein the smallest cross-sectional dimension of the foamed hook shaped microstructures is a width or thickness dimension and is about 50 microns or more, the foamed hook shaped microstructures have heights of generally 1000 microns or less, the ratio of the mean cell size of the discrete foam cells to the smallest cross-sectional dimension of the foamed hook shaped microstructures is 0.75 or less, the semicrystalline thermoplastic polymer is at least in part a high melt strength polypropylene having a melt strength in the range of 25 to 60 cN at 190° C. and the base layer is oriented in at least one direction.

2. The article of claim 1 wherein the smallest cross-sectional dimension of the foamed hook shaped microstructures is a width dimension of about 50 microns or more, the foamed hook shaped microstructures have heights of generally 750 microns or less, the ratio of the mean cell size of the discrete foam cells to the smallest cross-sectional dimension of the foamed hook shaped microstructures is 0.5 or less, the semicrystalline thermoplastic polymer is at least in part a high melt strength polypropylene having a melt strength of 30 to 55 cN at 190° C.

3. The article of claim 1 wherein the foamed hook shaped microstructures have a height ranging from 200 microns to 1000 microns.

4. The article of claim 1 wherein the ratio of the mean cell size of the discrete foam cells to the smallest cross-sectional dimension of the foamed hook shaped microstructures is 0.5 or less and the foamed hook shaped microstructures have a height ranging from 300 microns to 1000 microns.

5. The article of claim 1 wherein the foamed hook shaped microstructures have a maximum cross-sectional extent of 300 microns.

6. The article of claim 1 wherein the foamed hook shaped microstructures have a maximum cross-sectional extent of 200 microns.

7. The article of claim 1 wherein the base layer is a foam sheet.

8. The article of claim 7 wherein the foam sheet has a thickness of from 25 to 1000 microns.

9. The article of claim 7 wherein the foam sheet has a thickness of from 25 to 100 microns.

10. The article of claim 9 wherein the foam sheet has a softness of from 10 to 2000 Gurley units.

11. The article of claim 9 wherein the foam sheet has a softness of from 10 to 200 Gurley units.

12. The article of claim 7 wherein the foam sheet has a foam cell size of from 2 to 100 microns.

13. The article of claim 7 wherein the foam sheet has a foam cell size of from 5 to 50 microns and a foam cell size polydispersity from 1 to 2.

14. The article of claim 1 wherein the discrete foam cells have cell sizes of 100 microns or less.

15. The article of claim 1 wherein the foamed hook shaped microstructures are about 0.2 to 0.5 mm in height.

16. The article of claim 15 wherein the density of the foamed hook shaped microstructures is from 60 to 1000 hooks/cm².

17. The article of claim 15 wherein the foamed look shaped microstructures have a stem portion and a head portion.

18. The article of claim 17 wherein the head portion is a capped head which extends out from the stem on at least one side by 0.01 to 0.3 mm.

19. The article of claim 1 wherein the base layer is foamed.

20. The article of claim 1 wherein the base layer is non-foamed.

21. The article of claim 1 wherein the foamed hook shaped microstructures are soft to the touch.

* * * * *

UNITED STATES PATENT AND TRADEMARK OFFICE
CERTIFICATE OF CORRECTION

PATENT NO. : 7,883,769 B2  
APPLICATION NO. : 10/464215  
DATED : February 8, 2011  
INVENTOR(S) : Jayshree Seth Page 1 of 1

It is certified that error appears in the above-identified patent and that said Letters Patent is hereby corrected as shown below:

In the Specifications:

<u>Column 5</u>
Line 36, after "wollastonite" insert --.--.

<u>Column 6</u>
Line 43, delete "coalescense" and insert in place thereof --coalescence--.

<u>Column 8</u>
Line 47, delete "coalescense." and insert in place thereof --coalescence.--.

In the Claims:

<u>Column 18</u>
Line 47, Claim 17, delete "look" and insert in place thereof --hook--.

Signed and Sealed this
Twenty-ninth Day of March, 2011

David J. Kappos
*Director of the United States Patent and Trademark Office*